US00PP35748P2

(12) United States Plant Patent
Valin

(10) Patent No.: US PP35,748 P2
(45) Date of Patent: Apr. 16, 2024

(54) ***WEIGELA* PLANT NAMED 'TMWG18-04'**

(50) Latin Name: *Weigela florida*
Varietal Denomination: TMWG18-04

(71) Applicant: Branded Garden Products Ltd., Ipswich (GB)

(72) Inventor: Charles Valin, Ipswich (GB)

(73) Assignee: Branded Garden Products Ltd., Ipswich (GB)

( * ) Notice: Subject to any disclaimer, the term of this patent is extended or adjusted under 35 U.S.C. 154(b) by 0 days.

(21) Appl. No.: 18/186,169

(22) Filed: Mar. 19, 2023

(51) Int. Cl.
*A01H 6/00* (2018.01)
*A01H 5/02* (2018.01)

(52) U.S. Cl.
USPC ..... Plt./226

(58) Field of Classification Search
USPC ..... Plt./226
CPC ..... A01H 6/00; A01H 5/02
See application file for complete search history.

*Primary Examiner* — Keith O. Robinson
(74) *Attorney, Agent, or Firm* — Weatherly IP Solutions, LLC; James M. Weatherly

(57) ABSTRACT

A new cultivar of *Weigela* plant named 'TMWG18-04' that is characterized by its compact upright vase-shaped growth habit, achieving a height and width of 60 cm-65 cm after two years of growth. The foliage of 'TMWG18-04' is bright yellow-green in color and the inflorescences of 'TMWG-18-04' consist of flowers borne in cymes ranging from eight to twelve flowers per cyme. Each flower of 'TMWG18-04' consists of five petals with mid-pink flared lobes arranged around red centers.

2 Drawing Sheets

Genus and species: *Weigela florida.*
Variety denomination: 'TMWG18-04'.

BACKGROUND OF THE NEW PLANT

The present invention relates to a new and distinct cultivar of *Weigela*, grown as an ornamental plant for use in the garden and landscape. The new cultivar is known botanically as *Weigela florida* and will be referred to hereinafter by the cultivar name 'TMWG18-04'.

'TMWG18-04' originated from a *Weigela* breeding program which the inventor carried out at the inventor's nursery in Ipswich, United Kingdom. The inventor had assembled a collection of *Weigela* varieties (both commercial varieties and inventor's proprietary selections). After hand pollination between many of the assembled plants, seeds were collected, sown, grown on and planted in the field for evaluation. The identities of the parents of 'TMWG18-04' are unknown.

The new cultivar 'TMWG18-04' was selected in the field in 2018 for its combination of compact plant habit, very dark foliage and early production of large pink-purple tubular flowers with wide mouths.

The inventor first asexually reproduced 'TMWG18-04' in 2018 by the method of softwood cuttings. The inventor has determined that the unique characteristics of 'TMWG18-04' are stable and reproduce true to type in successive generations of asexual reproduction.

SUMMARY

The following traits have been repeatedly observed and represent the characteristics of the new *Weigela* cultivar 'TMWG18-04'. 'TMWG18-04' has not been tested under all possible conditions and phenotypic differences may be observed with variations in environmental, climatic and cultural conditions.

1. 'TMWG18-04' exhibits a compact upright vase-shaped growth habit.
2. After two years of growth in a 3-gallon container, plants of 'TMWG18-04' achieve a height and width of 60 cm to 65 cm.
3. The foliage of 'TMWG18-04' is bright yellow-green in color.
4. The inflorescences of 'TMWG18-04' consist of flowers borne in cymes ranging from eight to twelve flowers per cyme.
5. The flowers of 'TMWG18-04' consist of five petals with flared free petal lobes which are mid-pink in color.
6. The flowers of 'TMWG18-04' exhibit red centers.
7. 'TMWG18-04' flowers profusely in late spring and early summer and sporadically through mid and late summer.
8. 'TMWG18-04' grows well in moist well-drained soils in full sun to partial shade.
9. 'TMWG18-04' is hardy at least to USDA Zone 5.

BRIEF DESCRIPTION OF THE PHOTOGRAPHS

The accompanying color photographs illustrate the overall appearance of the new *Weigela* variety 'TMWG18-04' showing colors as true as it is reasonably possible to obtain in colored reproductions of this type. Colors in the photographs may differ from the color values cited in the detailed botanical description, which accurately describe the actual observed colors of the new variety 'TMWG18-04'.

Figure 1:
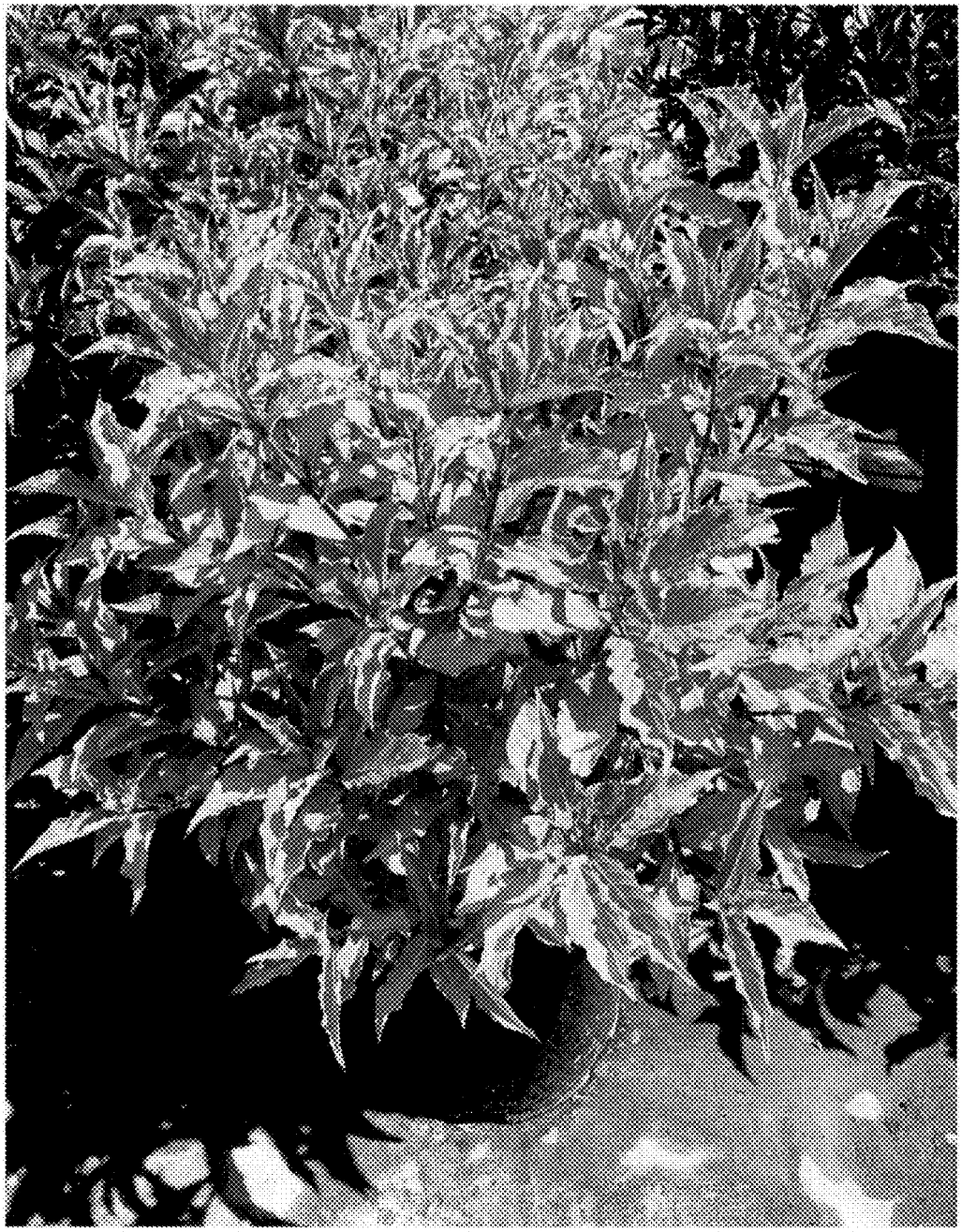

FIG. 1 depicts a two year old plant of 'TMWG18-04' in early spring before flowering.

Figure 2:
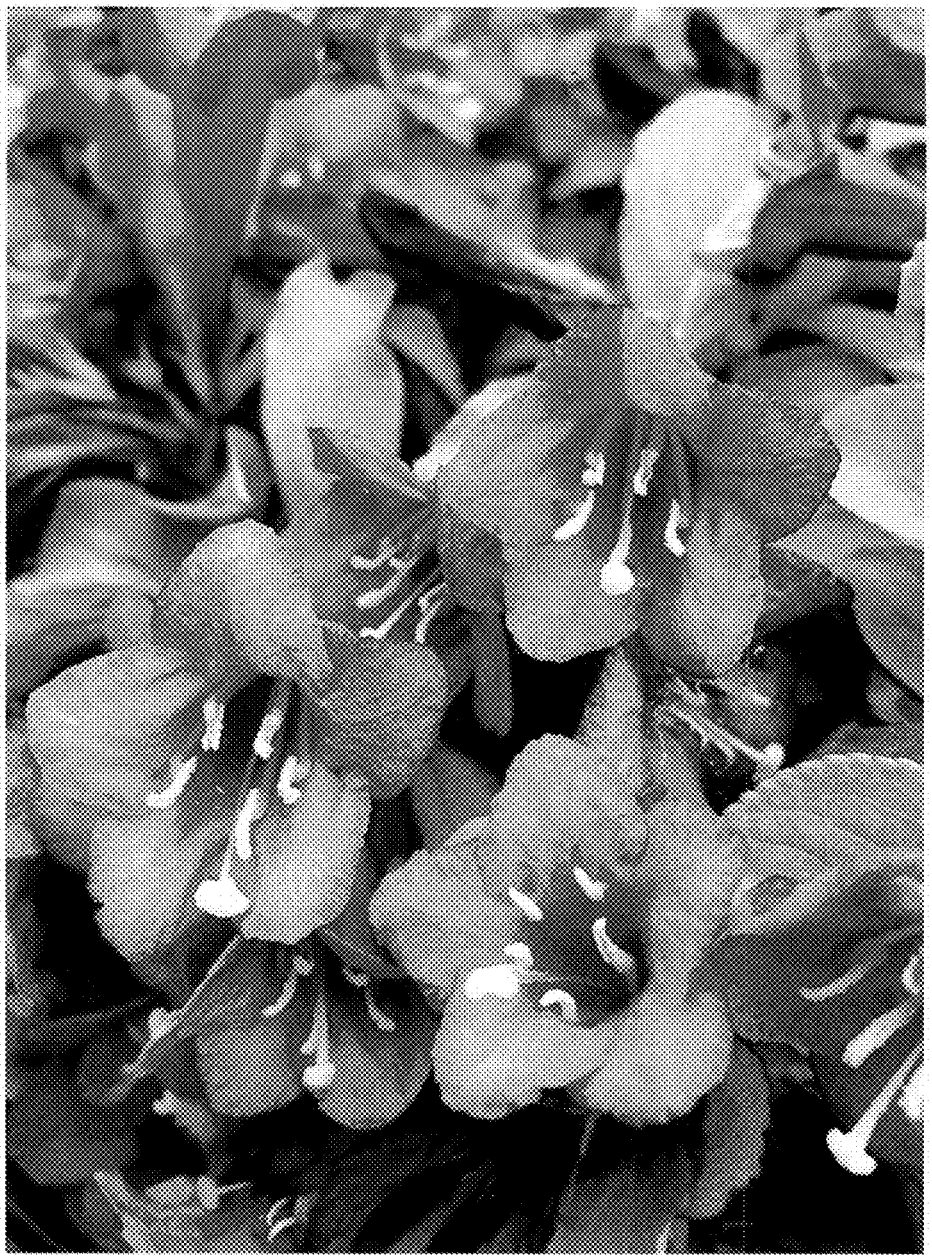

FIG. 2 presents a close-up view of the inflorescence of 'TMWG18-04' in early summer when the plant is in peak bloom.

Both photographs were taken in Santa Barbara, California where the plants were growing entirely outdoors under light shade cloth. No chemicals were used to treat the plants.

BOTANICAL DESCRIPTION OF THE PLANT

The following is a detailed description of the new cultivar 'TMWG18-04'. Data was collected in mid-summer from a two-year old plant grown in 3-gallon container under light shade in Santa Barbara, California. The color determinations are in accordance with the 2007 edition of The Colour Chart of The Royal Horticultural Society, London, England, except where general color terms of ordinary dictionary significance are used. No chemicals were used to treat the plants.

Botanical classification: *Weigela.*

*Variety.*—'TMWG18-04'.

*Species.—Florida.*

Parentage:

*Female parent.*—Unknown.

*Male parent.*—Unknown.

Plant description:

*Growth habit.*—Compact, upright, vase-shaped.

*Use.*—In containers and in the landscape.

*Suitable container sizes.*—1 to 3 gallon containers.

*Dimensions in second year in a 3-gallon container.*—60 cm to 65 cm in height and width.

*Hardiness.*—At least hardy to USDA Zone 5.

*Propagation.*—Semi-ripe stem cuttings.

*Time to initiate roots.*—4 to 5 weeks are required to produce roots on an initial cutting.

*Crop time.*—9-10 months to produce a first year flowering plant in a one gallon container, and two years to produce a fully filled out flowering plant in a 3 gallon container.

*Root system.*—Fibrous.

*Light.*—Plant in full sun or light shade.

*Soil.*—Plant in moist well-drained soil.

*Type.*—Deciduous shrub.

*Seasonal interest.*—Bright yellow-green foliage from spring to fall and profuse pink flowers with red eyes from late spring into early summer. Flowering then subsides and continues into mid-summer to late-summer.

Stem:

*Shape.*—Terete.

*Dimensions.*—3 cm in length, 1.5 cm in diameter at soil level.

*Color.*—161C.

*Surface.*—Lignified in second year, rough, glabrous, lenticels present.

*Lenticels.*—spaced approximately 5 mm apart, raised 0.5 mm above stem surface, narrowly elliptic, 1.5 mm-3 mm in length, 0.5 mm-1 mm in width, color 161C except lenticular margin 165A.

Branches:

*Description.*—All branches arise from the base of the plant, at or below the initial pinch or stopping of the first growth.

*Quantity.*—Approximately 20 basal branches.

*Branch stem length.*—50 cm to 55 cm in length. First leaves borne at 20 cm from stem base.

*Branch stem diameter.*—6 mm below first leaves, 4 mm-5 mm within the leaf-bearing section of the stem.

*Shape.*—Terete.

*Internode length.*—Varies between 2.5 cm and 5 cm.

*Stem color (below first leaves).*—162B.

*Stem color (within leaf-bearing section and at apex.*—181A.

*Surface.*—Smooth, pubescent, hairs fine and short, less than 0.5 mm in length, hair color 156B.

*Lenticels.*—Occasionally present towards base of older stems only, very slightly raised, elliptic, 2 mm in length, 1 mm in width, color 161C except faint lenticular margin 165A.

Foliage:

*Leaf arrangement.*—Opposite.

*Leaf division.*—Simple.

*Leaf shape.*—Ovate, longitudinally inwardly curved.

*Leaf attachment.*—Short petiolate.

*Petioles.*—Shape: Sulcate, adaxial surface concave. Dimensions: Up to 4 mm in length and 2 mm in width. Color: Ranges between 150B and 150C. Margins: Lightly pubescent, hairs approximately 0.5 mm in length. Margin color: Red 42A, hairs 42A.

*Leaf dimensions.*—80 mm in length, 32 mm in width.

*Leaf surface (adaxial surface).*—Glabrous, semi-glossy.

*Leaf surface (abaxial surface).*—Glabrous, dull, matte.

*Leaf color (adaxial surface).*—Ranges between N144C and 144A.

*Leaf color (abaxial surface).*—Ranges between 145B and 145C.

*Leaf apex.*—Acute.

*Leaf base.*—Cuneate.

*Leaf margin.*—Undulating and serrate, teeth 1 mm-1.5 mm apart, depth 0.5 mm, glabrous.

*Leaf venation pattern.*—Pinnate.

*Veins (adaxial surface).*—Slightly depressed, color as leaf, N144C-144A.

*Veins (abaxial surface).*—Midrib raised especially towards leaf base. Midrib and primary vein color 160D, secondary vein color N200B.

Inflorescence:

*Inflorescence form.*—Cymose.

*Quantity of inflorescences per plant (late spring, early summer).*—Approximately 20.

*Quantity of flowers per inflorescence.*—8-12.

Flowers:

*Flower shape.*—Salverform.

*Flower aspect.*—Outward and upward facing.

*Length of flower.*—36 mm.

*Diameter of flower (at flower tube apex).*—17 mm.

*Bud.*—Shape: Tubulate. Dimensions (including corolla tube): 30 mm in length (including corolla tube), 9 mm in diameter (towards bud apex immediately prior to opening). Color: 64A. Surface: Glabrous, matte.

*Peduncle.*—Dimensions: 17 mm in length and 1 mm in diameter. Shape: Terete. Color: 150B-150C. Surface: Glabrous.

*Calyx, sepals.*—Calyx shape: Funnelform. Calyx diameter: 6 mm measured across sepal apices. Sepals: 5 in number, fused towards and at base. Sepal dimensions: 8 mm-9 mm in length, 2 mm in width. Sepal color (both surfaces): N144B. Sepal surface (both surfaces): Matte, puberulent.

*Corolla.*—Shape: Tubulate. Dimensions: 30 mm in length (to base of petal lobes), 2 mm in diameter at base of petal lobes. Surface: Glabrous. Tube color: 64A (inner surface), 64B-64C (outer surface).

*Petals*.—Description: 5 petals, longitudinally fused then lobed and free, rotate, slightly overlapping. Lobe shape: Orbicular, reflexing with age. Lobe color (adaxial surface): 64B-64C at first opening, fading to 64C-64D as flower fully opens and as petal lobes become reflexed. Surface texture (adaxial surface): Lightly coarse, glabrous. Surface texture (abaxial surface): Smooth, glabrous.

Reproductive organs:

*Stamens*.—Quantity: 5, fused at base. Filament length: 18 mm-20 mm in length, of which basal 5 mm fused to corolla tube wall and 13 mm-15 mm free. Filament diameter: 0.75 mm-1.0 mm. Filament color: 63B except 62D immediately below anthers. Anthers: Elliptic, bifid, dorsifixed. Anther dimensions: 5 mm in length, 1 mm in width. Anther color: 162D. Pollen: Moderate amount, color NN155D.

*Pistils*.—Quantity: 1. Pistil length: 43 mm, of which approximately 13 mm protrudes beyond corolla tube. Style: Round, very slender, 39 mm in length and 0.5 mm in diameter, glabrous. Style color: 63B except 62D immediately below stigma. Stigma shape: Capitate, three-lobed, positioned approximately 5 mm above petal lobe apices. Stigma dimensions: 3 mm-4 mm in diameter, 2.5 mm in height. Stigma color: NN155B.

*Ovary*.—Minute, appears undeveloped.

Seed: None observed.

Susceptibility or resistance to pests and diseases: None.

COMPARISON WITH PARENT VARIETIES

The parents of 'TMWG18-04' are unknown. No comparison is available.

COMPARISON WITH KNOWN VARIETY

'TMWG18-04' may be compared with the widely grown *Weigela* variety 'Rubidor' (unpatented). Both 'TMWG18-04' and 'Rubidor' bear chartreuse colored yellow-green foliage and dark red flowers. However, the leaves of 'TMWG18-04' are lighter and brighter in color. In addition, whereas 'TMWG18-04' is a compact and low growing variety, 'Rubidor' grows to at least 1.5 m to 2 m in height.

I claim:

1. A new and distinct cultivar of *Weigela* Plant Named 'TMWG18-04' as described and illustrated herein.

* * * * *